United States Patent
Kuroda

(10) Patent No.: US 6,270,701 B1
(45) Date of Patent: Aug. 7, 2001

(54) METHOD FOR FABRICATING REMOVABLE DENTURE PROTHESIS USING INJECTION MOLDING

(75) Inventor: Hirofumi Kuroda, Torrance, CA (US)

(73) Assignee: G&H Dental Arts, Inc., Torrance, CA (US)

( * ) Notice: Subject to any disclaimer, the term of this patent is extended or adjusted under 35 U.S.C. 154(b) by 0 days.

(21) Appl. No.: 09/114,197

(22) Filed: Jul. 13, 1998

(51) Int. Cl.⁷ .................................................. A61C 13/10
(52) U.S. Cl. ........................ 264/18; 264/221; 264/222; 264/313; 264/318; 264/338; 264/DIG. 30; 264/DIG. 44
(58) Field of Search ..................................... 264/221, 222, 264/313, 318, 16, 17, 338, DIG. 30, DIG. 44, 18; 425/2; 249/54, 55, 61

(56) References Cited

U.S. PATENT DOCUMENTS 4,583,947  * 4/1986 Hazar ................................... 433/171
4,892,478  * 1/1990 Tateosian et al. ....................... 433/6
5,607,628  * 3/1997 Palazzolo ............................... 264/18

* cited by examiner

Primary Examiner—Jan H. Silbaugh
Assistant Examiner—Suzanne E. McDowell
(74) Attorney, Agent, or Firm—Irving Keschner

(57) ABSTRACT

A method for forming removable dentures using injection molding techniques wherein a cyanoacrylate base material is applied to the sides of the denture teeth, an activator or accelerator compound being sprayed onto the deposited base material whereby the base material is rapidly cured. The denture is then placed in the lower half of a mold, or flask, and a plurality of sprues are positioned therein. The upper flask portion is then attached to the lower half and the assembled flask is then invested with plaster material. The activated gel enables the teeth to be retained in position in the lower half of the flask. The flask is then placed in hot or boiling water and then deflasked to remove the melted wax. The flask is then reassembled and polymer injected therein filling the areas previously occupied by the wax. After the polymer is cured, the prothesis is removed, polished and then returned to the dentist.

5 Claims, 3 Drawing Sheets

METHOD FOR FABRICATING REMOVABLE DENTURE PROTHESIS USING INJECTION MOLDING

BACKGROUND OF INVENTION

1. Field of Invention

The present invention provides a method for maintaining denture teeth in position in an injection flask during the investment process. In particular, a cyanoacrylate based compound is applied to the sides of the denture teeth and then sprayed with an accelerator to harden the gel.

2. Description of the Prior Art

Techniques for fabricating removable partial and full dentures have been utilized for many years by dental laboratories throughout the United States and around the world. For example, Dentsply International Inc., York, Pennsylvania markets a SUCCESS® injection system for creating a full denture appliance, or prothesis, utilizing LUCITONE 199® denture resin. GC Lab Technologies Inc., Lockport, Ill. provides a Acron denture injection system for fabricating denture appliances which enables a flask invested with acrylic polymer to be cured using a conventional microwave appliance.

U.S. Pat. Nos. 4,378,213 and 4,529,384 disclose and claim the use of cyanoacrylate compounds for dental modeling of non-removable prothesis, such as crowns, porcelain jacket crowns, indexed multiple crowns and the like.

The above-noted references do not address the problems of retaining plastic or porcelain denture teeth in the mold, or flask, during boil-out and/or injection and/or polymerization. In this regard, teeth have a tendency to pop-out during boil-out and/or the teeth to move during injection or polymerization. This in turn requires teeth repair or remake, increasing the time and cost of producing the prothesis.

What is desired is to provide a denture injection system wherein the denture teeth do not pop out or move during boil-out and/or acrylic injection and acrylic polymerization.

SUMMARY OF THE PRESENT INVENTION

The present invention provides a method for forming removable dentures using injection molding techniques wherein a cyanoacrylate base material is applied to the denture teeth, an activator or accelerator compound being sprayed onto the deposited base material whereby the base material is rapidly cured. The denture is then placed in the lower half of a mold, or flask, and a plurality of sprues are positioned therein. The upper flask portion is attached to the lower half and the assembled flask is then invested with plaster material. The activated gel enables the teeth to be retained in position in the lower half of the flask. The flask is then placed in hot or boiling water and then deflasked to remove the melted wax. The flask is then reassembled and polymer injected therein filling the areas previously occupied by the wax. After the polymer is cured, the prothesis is removed, polished and then returned to the dentist.

The present invention thus provides a technique for securing plastic or porcelain teeth in a flask during preparation of the dental prothesis, thus avoiding the costs involved in replacing or aligning teeth that have moved during the prothesis fabrication process.

BRIEF DESCRIPTION OF THE DRAWING

For a better understanding of the invention, as well as other objects and further features thereof, reference is made to the following description which is to read in conjunction with the accompanying drawing wherein.

DESCRIPTION OF THE INVENTION

Figure 1:
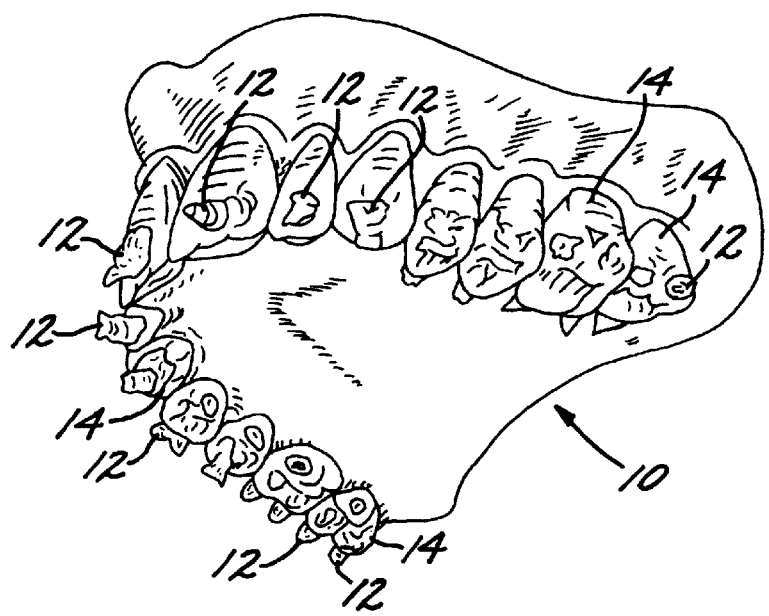
FIG. 1 illustrates a full denture with gel applied to plastic denture teeth.

Since the basic denture fabrication process is well-known and conventional, only a brief description will be set forth hereinafter in order to place the present invention in proper perspective.

In particular, the partial or full denture/impression or master cast received from the dentist is poured up with lab stone (gypsum). After the removable prothesis has been evaluated, designed and fabricated for a teeth set-up and try-in in wax, the prothesis is sent back to the dentist for approval. After approval, the wax-up is ready for final processing. In accordance with the teachings of the present invention, a thick base gel is placed on the denture teeth and thereafter an activator is sprayed thereon to cure (harden) the gel (details of this step will be set forth hereinbelow). The wax-up is then placed in the bottom half of a flask and invested with stone (plaster or gypsum). The investment is allowed to harden and then injection sprues are positioned in the bottom flask for the polymer material which will replace the wax. The gel is fabricated from a cyanoacrylate base with a high viscosity such as that disclosed in U.S. Pat. Nos. 4,378,213 and 4,529,384, the teachings of which necessary for an understanding of the present invention being incorporated herein by reference. The dynamic viscosity of the cyanoacrylate compound is maintained in the range between 30,000 centipoise/inch$^2$ and 300,000 centipoise/inch$^2$ to provide a gel that retains its basic shape when applied to the denture teeth. A gel having the desired characteristics is distributed by Alteco USA, Inc., Torrace, Calif. A conventional actuator can be used, such as that disclosed in the above-noted patents. The top portion of the flask is attached to the bottom half and the flask is invested with stone through an opening formed in the top half portion of the flask. The flask portions are then separated and placed in hot or boiling water to melt the wax. A separator is placed on the stone portions of the flask interior to prevent acrylic from adhering thereto. The flask portions are then joined together and acrylic injected into the flask to replace the missing wax.

It should be noted at this point that the hardened gel retains plastic or porcelain denture teeth in the flask during boil-out and/or injection and/or polymerization. By preventing teeth from popping out during boil out, there is no need to glue the teeth back into the flask as required in the prior art. Further, the teeth are prevented from moving during injection or polymerization, thus ensuring no change in the vertical dimension. Since the teeth can not move during injection or polymerization, repair or remake of the prothesis is not necessary, reducing the costs of prosthesis fabrication.

After the acrylic sets, the flask is separated, the prothesis is broken out (removed) from the bottom flask portion, polished and then returned to the dentist.

When the gel is applied to the denture teeth, undercuts and/or extensions are created on the teeth. The liquid activator is sprayed on the gel to cure (harden) it. After investing the teeth wax-up, the teeth are retained in the stone investment due to the gel. When the wax is boiled out with hot water, the teeth are retained in the flask. A thin coat of liquid separator is applied to the surfaces of the stone investment on the top and bottom halves of the flask. When acrylic polymer is injected into the flask, the teeth are retained in the flask.

The gel of the present invention improves upon the prior art cyanoacrylate based gels in that it has a thicker base (greater viscosity) allowing undercuts and/or extensions to be created whereas the prior art gels are less viscous and would run if used to replace the gel of the present invention.

Figure 2:
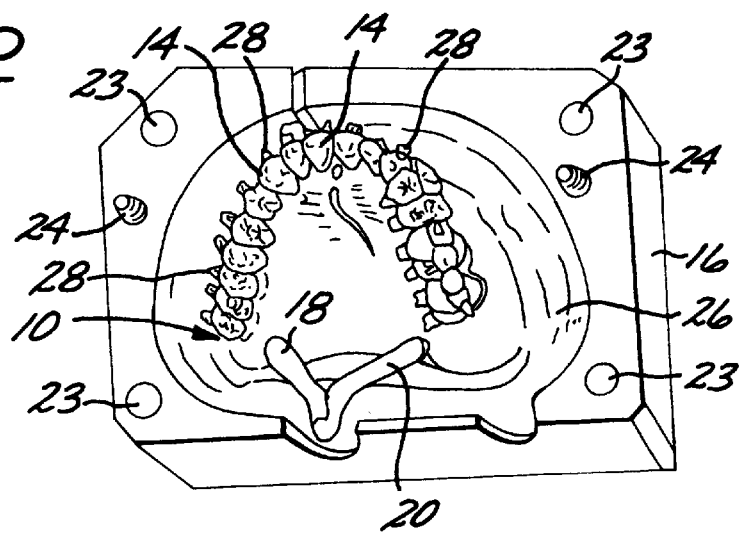
FIG. 2 illustrates a full denture in a bottom half of a flask with gel applied to plastic teeth before the top half of the flask is closed.
Figure 3:
FIG. 3 illustrates application of gel to one of the teeth shown in FIG. 1.
Figure 4:
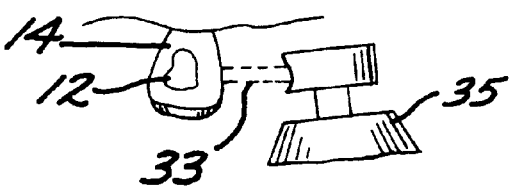
FIG. 4 illustrates application of an accelerator compound to the tooth shown in FIG. 2.

FIG. 1 illustrates a full upper denture 10 having dabs of gel 12 applied to plastic teeth 14. FIG. 2 illustrates the full denture of FIG. 1 positioned in the bottom, or lower, flask portion 16 of a flask, plastic injection sprues 18 and 20 being positioned within flask portion 16 as shown. Flask portion 16 has four threaded apertures for receiving fasteners 23, such as bolts, to secure the top flask portion (not shown) to bottom flask portion 16. Two threaded fasteners 24 are provided in bottom flask portion 16 to engage threaded apertures formed in the upper flask portion. The bottom flask portion 16 is shown as having been invested with stone material 26. Cured, or set, gel 28 is shown applied to the sides of denture teeth 14. FIG. 3 illustrates the gel application procedure for one of the teeth 14 shown in FIG. 2. In particular, the gel 12 is applied as small drops or dabs (approximately 0.1 grams per drop or dab) using a conventional tube applicator or storage container 31. Once the desired quantity of the gel is properly dispensed on the sides of the denture teeth, accelerator 33 is sprayed onto the gel area using a conventional aerosol or atomizing container 35 or pump spray as illustrated in FIG. 4. On application of the accelerator, the gel 12 begins to set or cure and becomes a hardened mass within three or four minutes.

Figure 8:
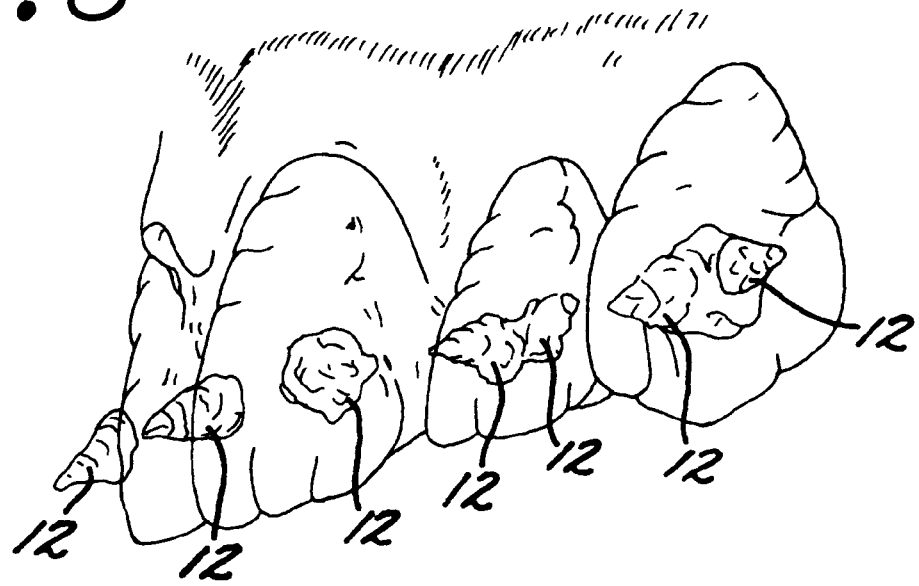
FIG. 8 illustrates the application of gel to anterior plastic teeth.

The steps of applying the gel 12 to specific areas of the denture teeth 14, both plastic and porcelain, is as follows:

1. For anterior teeth, one or two (plastic teeth) dabs of gel 12 are applied to the labial surface, application of gel on then incisal areas being avoided. The right three teeth shown in FIG. 3 are porcelain anterior teeth; FIG. 8 shows a denture comprising anterior plastic teeth.

Figure 7:
FIG. 7 illustrates the application of gel to posterior plastic teeth.

2. For posterior teeth, two or three dabs of gel are preferred. For bicuspids, two dabs should be used, one on the buccal surface and one on the lingual surface. On the molars, three dabs are preferred; one dab on the mesial buccal surface, one dab on the distal buccal surface and one dab on the lingual surface (FIG. 7 illustrates posterior plastic teeth).

Figure 5:
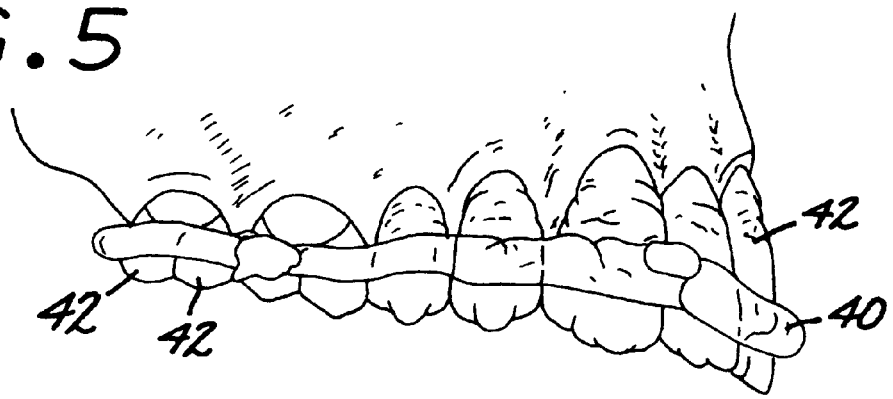
FIG. 5 is a side view illustrating gel applied to porcelain teeth.
Figure 6:
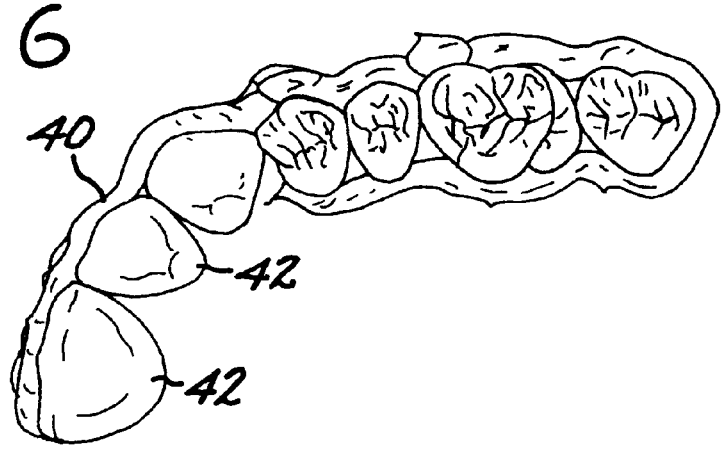
FIG. 6 is a top view illustrating gel applied to porcelain teeth.

3. For porcelain teeth, gel is applied continuously to the anterior teeth from tooth to tooth on the labial surface; in the case of bicuspids and molars, a continuous application of gel from tooth to tooth is preferred on the buccal and lingual surfaces. FIG. 5 is a side view showing gel 40 applied continuously to porcelain teeth 42 (left four teeth are posterior porcelain teeth); FIG. 6 is a top view of the porcelain denture teeth 42 shown in FIG. 5 (left three teeth are anterior teeth; the four right hand teeth are posterior teeth).

It should be noted that since porcelain has a hard high glaze surface, cyanoacrylate tends not to bond easily to the porcelain surface. Thus porcelain teeth require more gel than plastic teeth to ensure teeth retention in the flask.

It should be noted that the present invention can be used with a prothesis fabrication process wherein deflasking is not necessary.

While the invention has been described with reference to its preferred embodiments, it will be understood by those skilled in the art that various changes may be made and equivalents may be substituted for elements thereof without departing from the true spirit and scope of the invention. In addition, many modifications may be made to adapt a particular situation or material to the teaching of the invention without departing from its essential teachings.

What is claimed is:

1. A method for fabricating a removable denture comprising the steps of;

applying a thick base gel on selected positions on teeth positioned in a denture wax-up;

applying an activator to the applied base gel to harden the gel;

placing the wax-up in the bottom half of a flask;

investing the flask with a stone material that hardens after a predetermined time period;

allowing said stone material to harden;

positioning the top portion of the flask on the bottom flask half;

investing the assembled flask with said stone material;

separating the flask portions;

placing injection sprues in the lower half of said flask;

allowing said stone material to harden;

melting the denture wax material;

joining the flask portions;

injecting acrylic resin into said flask;

curing the acrylic resin;

separating the flask portions; and removing the denture from the bottom flask portion.

2. The method of claim 1 wherein the viscosity of said gel is in the range from 30,000 centipoise/inch$^2$ to about 300,000 centipoise/inch$^2$.

3. The method of claim 1 wherein said gel prevents said denture teeth from moving during the separation of said first and second flask portions.

4. The method of claim 1 wherein said teeth are fabricated from porcelain and said gel is placed continuously along certain of said teeth.

5. The method of claim 1 wherein said teeth are fabricated from plastic and said gel is applied to said plastic teeth in dabs.

* * * * *